US00PP30314P3

(12) United States Plant Patent
Ruigrok

(10) Patent No.: US PP30,314 P3
(45) Date of Patent: Mar. 26, 2019

(54) ***DAHLIA* PLANT NAMED 'FERANGEL'**

(50) Latin Name: *Dahlia hybrida*
Varietal Denomination: Ferangel

(71) Applicant: Sanne Helena Ruigrok, Beinsdorp (NL)

(72) Inventor: Sanne Helena Ruigrok, Beinsdorp (NL)

(73) Assignee: Fetura B.V., Hillegom (NL)

( * ) Notice: Subject to any disclaimer, the term of this patent is extended or adjusted under 35 U.S.C. 154(b) by 0 days.

(21) Appl. No.: 15/732,361

(22) Filed: Oct. 30, 2017

(65) Prior Publication Data

US 2018/0124979 P1 May 3, 2018

Related U.S. Application Data

(60) Provisional application No. 62/496,883, filed on Oct. 31, 2016.

(51) Int. Cl.
*A01H 5/02* (2018.01)

(52) U.S. Cl.
USPC ..... Plt./321
CPC ..... *A01H 5/02* (2013.01)

(58) Field of Classification Search
USPC ..... Plt./321
See application file for complete search history.

*Primary Examiner* — Keith O. Robinson
(74) *Attorney, Agent, or Firm* — C. A. Whealy

(57) ABSTRACT

A new and distinct cultivar of *Dahlia* plant named 'Ferangel', characterized by its compact, upright and mounding plant habit; moderately vigorous growth habit; freely branching habit; dark green-colored leaves; freely flowering habit; and double type inflorescences with white-colored ray florets.

1 Drawing Sheet

Botanical designation: *Dahlia hybrida.*
Cultivar denomination: 'FERANGEL'.

BACKGROUND OF THE INVENTION

The present invention relates to a new and distinct cultivar of *Dahlia* plant, botanically known as *Dahlia hybrida*, previously known as 'Angel' and hereinafter referred to by the name 'Ferangel'.

The new *Dahlia* plant is a product of a planned breeding program conducted by the Inventor in Hillegom, The Netherlands. The objective of the breeding program is to create new strong *Dahlia* plants with numerous double inflorescences.

The new *Dahlia* plant originated from a cross-pollination in Hillegom, The Netherlands in June, 2012 of a proprietary selection of *Dahlia hybrida* identified as code name DEC, not patented, as the female, or seed, parent with *Dahlia hybrida* 'Madahlia', not patented, as the male, or pollen, parent. The new *Dahlia* plant was discovered and selected by the Inventor as a single flowering plant from within the progeny of the stated cross-pollination in a controlled greenhouse environment in Hillegom, The Netherlands in September, 2013.

Asexual reproduction of the new *Dahlia* plant by vegetative terminal cuttings in a controlled greenhouse environment in Hillegom, The Netherlands since October, 2013 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Ferangel'. These characteristics in combination distinguish 'Ferangel' as a new and distinct *Dahlia* plant:

1. Compact, upright and mounding plant habit.
2. Moderately vigorous growth habit.
3. Freely branching habit.
4. Dark green-colored leaves.
5. Freely flowering habit.
6. Double type inflorescences with white-colored ray florets.

Compared to plants of the female parent selection, plants of the new *Dahlia* differ primarily in the following characteristics:

1. Plants of the new *Dahlia* are more compact than plants of the female parent selection.
2. Plants of the new *Dahlia* have smaller inflorescences than plants of the female parent selection.

Compared to plants of the male parent, 'Madahlia', plants of the new *Dahlia* differ primarily in the following characteristics:

1. Plants of the new *Dahlia* are larger than plants of the 'Madahlia'.
2. Plants of the new *Dahlia* are more freely branching than plants of 'Madahlia'.
3. Inflorescences of plants of the new *Dahlia* are more fully double than inflorescences of plants of 'Madahlia'.

Plants of the new *Dahlia* can be compared to plants of *Dahlia hybrida* 'BKDAWHT', disclosed in U.S. Plant Pat.

No. 24,919. In side-by-side comparisons, plants of the new *Dahlia* differ primarily from plants of 'BKDAWHT' in the following characteristics:

1. Plants of the new *Dahlia* are larger than plants of 'BKDAWHT'.
2. Leaves of plants of the new *Dahlia* have more pointed apices than leaves of plants of 'BKDAWHT'.
3. Inflorescences of plants of the new *Dahlia* are more fully double than inflorescences of plants of 'BKDAWT'.
4. Stock plants of the new *Dahlia* produce more vegetative terminal cuttings than Stock plants of 'BKDAWHT'.

BRIEF DESCRIPTION OF THE PHOTOGRAPH

The accompanying photograph illustrates the overall appearance of the new *Dahlia* plant showing the colors as true as it is reasonably possible to obtain in colored reproductions of this type. Colors in the photograph may differ slightly from the color values cited in the detailed botanical description which accurately describe the colors of the new *Dahlia* plant.

The photograph is a side perspective view of a typical flowering plant of 'Ferangel' grown in a container.

DETAILED BOTANICAL DESCRIPTION

The aforementioned photographs and following observations and measurements describe plants grown during the summer in 1.5-liter containers in a glass-covered greenhouse in DeKwakel, The Netherlands and under cultural practices typical of commercial potted *Dahlia* production. During the production of the plants, day temperatures ranged from 16° C. to 23° C. and night temperatures ranged from 13° C. to 18° C. Plants were 16 and 20 weeks old when the description and photograph, respectively, were taken. In the following description, color references are made to The Royal Horticultural Society Colour Chart, 2015 Edition, except where general terms of ordinary dictionary significance are used.

Botanical classification: *Dahlia hybrida* 'Ferangel'.

Parentage:

*Female, or seed, parent*.—Proprietary selection of *Dahlia hybrida* identified as code name DEC, not patented.

*Male, or pollen, parent*.—*Dahlia hybrida* 'Madahlia', not patented.

Propagation:

*Type*.—By vegetative terminal cuttings.

*Time to initiate roots, summer*.—About six days at temperatures about 22° C. to 25° C.

*Time to initiate roots, winter*.—About eight days at temperatures about 18° C.

*Time to produce a rooted plant, summer*.—About three weeks at temperatures about 22° C. to 25° C.

*Time to produce a rooted plant, winter*.—About five weeks at temperatures about 18° C.

*Root description*.—Thick, fleshy; typically close to white in color, actual color of the roots is dependent on substrate composition, water quality, fertilizers, substrate temperature and age of roots; tuber development has not been observed on plants of the new *Dahlia* to date.

*Rooting habit*.—Moderately freely branching; medium density.

Plant description:

*Plant and growth habit*.—Compact, upright and mounded plant form; broad inverted triangle; freely branching habit with about four primary lateral branches each with about two secondary lateral branches developing per plant; inflorescences held above and beyond the foliar plane on strong peduncles; moderately vigorous growth habit and moderate growth rate.

*Plant height, soil level to top of foliar plane*.—About 15.4 cm.

*Plant height, soil level to top of floral plane*.—About 24.5 cm.

*Plant diameter or spread*.—About 22.9 cm.

*Lateral branches*.—Length: About 7.2 cm. Diameter: About 4 mm. Internode length: About 1 cm to 5.3 cm. Strength: Moderately strong. Aspect: Primary laterals, about 15° from vertical; secondary laterals, about 40° from primary lateral axis. Texture and luster: Smooth, glabrous; glossy. Color, developing and developed: Close to 144A; at the internodes, close to 146B.

Leaf description:

*Arrangement*.—Opposite; simple or compound with three leaflets.

*Simple leaf length*.—About 7.2 cm.

*Simple leaf width*.—About 5.4 cm.

*Compound leaf length*.—About 7.3 cm.

*Compound leaf width*.—About 7.5 cm.

*Terminal leaflet length*.—About 6.2 cm.

*Terminal leaflet width*.—About 3.9 cm.

*Lateral leaflet length*.—About 4.1 cm.

*Lateral leaflet width*.—About 2.4 cm.

*Simple leaf shape*.—Broadly ovate.

*Compound leaf shape*.—Broadly ovate in overall outline.

*Terminal and lateral leaflet shape*.—Ovate.

*Leaf and leaflet apex*.—Bluntly acute.

*Leaf and leaflet base*.—Attenuate.

*Leaf and leaflet margin*.—Coarsely dentate.

*Leaf and leaflet venation pattern*.—Pinnate.

*Leaf and leaflet texture and luster, upper surface*.—Slightly rugose; sparsely pubescent; slightly velvety; slightly glossy.

*Leaf and leaflet texture and luster, lower surface*.—Smooth (not rugose); sparsely pubescent; matte.

*Leaf and leaflet color*.—Developing leaves, upper surface: Close to 143A. Developing leaves, lower surface: Close to 143C. Fully expanded leaves, upper surface: Close to 137A to 137B; venation, close to 146A. Fully expanded leaves, lower surface: Close to between 138B and 191B; venation, close to 146B. Simple leaf petiole length: About 2.7 cm. Simple leaf petiole diameter: About 3 mm by 2.5 mm. Compound leaf petiole length: About 3.2 cm. Compound leaf petiole diameter: About 3 mm by 2.5 mm. Leaf and leaflet petiole strength: Moderately strong to strong. Leaf and leaflet petiole texture and luster, upper surface: Smooth, glabrous; matte. Leaf and leaflet petiole texture and luster, lower surface: Smooth, glabrous; slightly glossy. Leaf and leaflet petiole color, upper and lower surfaces: Close to 144A.

Inflorescence description:

*Appearance and arrangement*.—Double inflorescence form with ray and disc florets forming acropetally on a receptacle; inflorescences positioned above and beyond the foliar plane on strong peduncles; inflorescences face mostly upright to somewhat outwardly; freely flowering habit with about 24 inflorescences developing per plant.

*Fragrance*.—Faintly fragrant; sweet and pleasant.

*Time to flower*.—Plants begin flowering about 13 weeks after planting; plants flower continuously during the autumn and winter until frost in The Netherlands.

*Inflorescence and post-production longevity*.—Inflorescences maintain good substance for about ten days on the plant; ray and disc florets persistent; plants maintain good substance for five weeks as a container plant.

*Inflorescence buds*.—Height: About 9 mm. Diameter: About 9 mm. Shape: Globular. Texture and luster: Smooth, glabrous; glossy. Color: Close to 151D; towards the base, close to 144A to 144B.

*Inflorescence size*.—Diameter: About 6.5 cm. Depth (height): About 3 cm. Disc diameter: About 1 cm, mostly inconspicuous.

*Receptacles*.—Height: About 3 mm. Diameter: About 4.5 mm. Shape: Flattened globular. Color: Close to 145B.

*Ray florets*.—Quantity per inflorescence: About 70 arranged in about four whorls. Length: About 3 cm. Width: About 1.5 cm. Shape: Obovate; somewhat concave. Apex: Obtuse to rounded. Base: Attenuate. Margin: Entire. Aspect: Initially upright; with development, about 55° from vertical. Texture and luster, upper surface: Smooth, glabrous; velvety, slightly glossy. Texture and luster, lower surface: Smooth, glabrous; somewhat velvety, matte. Color: When opening, upper and lower surfaces: Initially, close to 4D becoming closer to 155A with development; at the base, close to 1B. Fully opened, upper surface: Close to 155A slightly tinged with close to 4D; at the base, close to 2B; venation, similar to lamina; colors do not fade with development. Fully opened, lower surface: Close to 155A slightly tinged with close to 4D; at the base, close to 2C; venation, close to between 4D and 155A; colors do not fade with development.

*Disc florets*.—Quantity per inflorescence: About 25 arranged in about three whorls. Length: About 1.3 cm. Diameter: About 4 mm. Shape: Tubular, elongated; apices acute. Texture and luster: Smooth, glabrous; glossy. Color, when opening, inner and outer surfaces: Apex, close to 13A; mid-section, close to 151D; base, close to 150D. Color, fully opened, inner and outer surfaces: Apex, close to 12A; mid-section, close to 151D; base, close to 150D; colors do not fade with development.

*Phyllaries*.—Quantity per inflorescence: About six to occasionally seven phyllaries arranged in about two whorls. Length: About 1.3 cm. Width: About 4 mm. Shape: Oblanceolate. Apex: Acute. Base: Cuneate. Margin: Entire. Texture and luster, upper and lower surfaces: Smooth, glabrous; moderately glossy. Color, upper and lower surfaces: Close to 143A.

*Peduncles*.—Length: About 5.7 cm. Diameter: About 2.5 mm. Aspect: Mostly upright. Strength: Strong. Texture and luster: Smooth, glabrous; glossy. Color: Close to 144B.

*Reproductive organs*.—Present on disc florets only. Androecium: Quantity per floret: Five. Filament length: About 4 mm. Filament color: Close to 150D. Anther shape: Narrowly oblong. Anther size: About 0.5 mm by 3 mm. Anther color: Close to 15A. Pollen amount: Scarce. Pollen color: Close to 17A. Gynoecium: Quantity per floret: One. Pistil length: About 1.1 cm. Style length: About 9 mm. Style color: Close to 150D. Stigma diameter: About 4 mm. Stigma shape: Cleft. Stigma color: Close to 151D. Ovary color: Close to 145D. Seeds and fruits: Seed and fruit development have not been observed on plants of the new *Dahlia* to date.

Disease & pest resistance: Plants of the new *Dahlia* have not been observed to be resistant to pathogens and pests common to *Dahlia* plants to date.

Temperature tolerance: Plants of the new *Dahlia* have been observed to tolerate high temperatures about 35° C. and to be suitable for USDA Hardiness Zones 9 to 11.

It is claimed:

1. A new and distinct *Dahlia* plant named 'Ferangel' as illustrated and described.

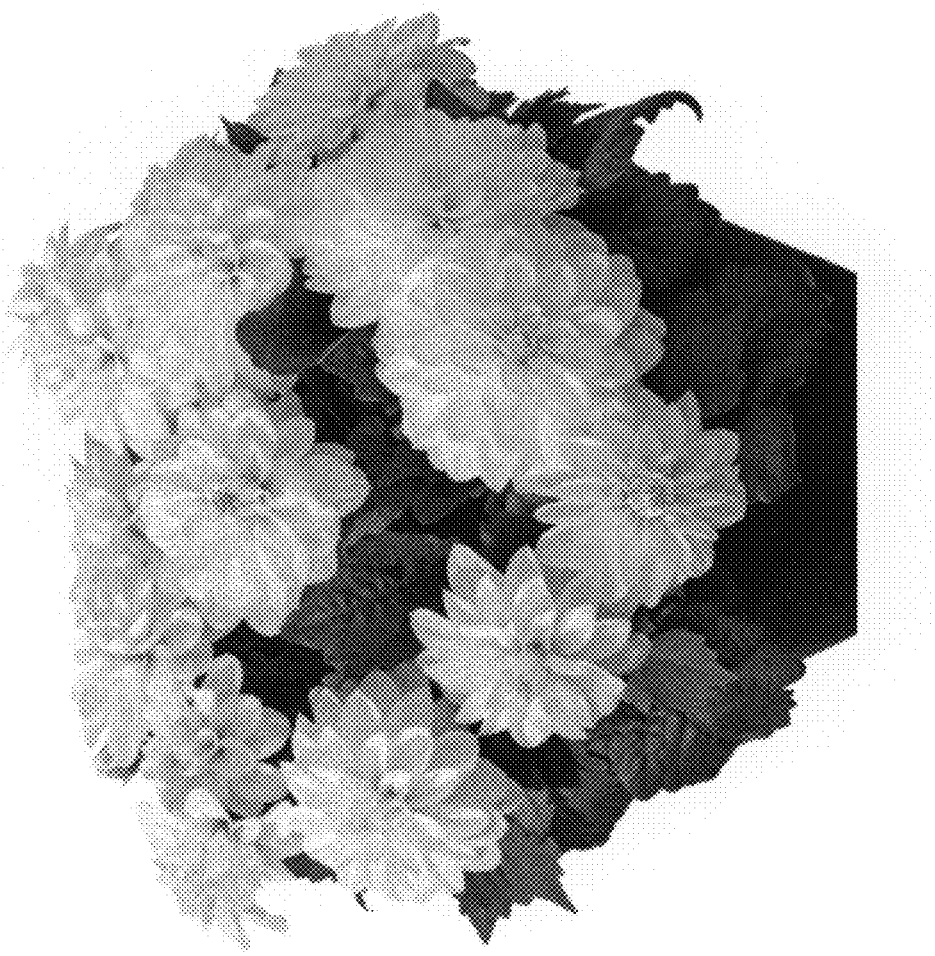

* * * * *